United States Patent
Stone et al.

(10) Patent No.: US 9,271,720 B2
(45) Date of Patent: Mar. 1, 2016

(54) STEERABLE SUTURE PASSING DEVICE

(75) Inventors: Kevin T. Stone, Winona Lake, IN (US);
Troy M. Walters, Plymouth, IN (US);
Ryan A. Kaiser, Leesburg, IN (US)

(73) Assignee: BIOMET SPORTS MEDICINE, LLC, Warsaw, IN (US)

( * ) Notice: Subject to any disclaimer, the term of this patent is extended or adjusted under 35 U.S.C. 154(b) by 2373 days.

(21) Appl. No.: 11/501,171

(22) Filed: Aug. 8, 2006

(65) Prior Publication Data

US 2007/0038230 A1    Feb. 15, 2007

Related U.S. Application Data

(60) Provisional application No. 60/707,238, filed on Aug. 11, 2005.

(51) Int. Cl.
| A61B 17/04 | (2006.01) |
| A61B 17/00 | (2006.01) |
| A61B 17/06 | (2006.01) |

(52) U.S. Cl.
CPC ......... *A61B 17/0482* (2013.01); *A61B 17/0485* (2013.01); *A61B 17/0401* (2013.01); *A61B 2017/003* (2013.01); *A61B 2017/00309* (2013.01); *A61B 2017/00314* (2013.01); *A61B 2017/00323* (2013.01); *A61B 2017/0404* (2013.01); *A61B 2017/0414* (2013.01); *A61B 2017/0417* (2013.01); *A61B 2017/06042* (2013.01)

(58) Field of Classification Search
CPC ........... A61B 17/0469; A61B 17/0482; A61B 17/0485; A61B 2017/00314; A61B 2017/003; A61B 2017/00309

USPC ................................. 606/144–148, 222–226
See application file for complete search history.

(56) References Cited

U.S. PATENT DOCUMENTS

| 4,926,860 | A |   | 5/1990  | Stice et al. |         |
| 4,984,581 | A |   | 1/1991  | Stice |         |
| 4,991,602 | A |   | 2/1991  | Amplatz et al. |         |
| 5,067,489 | A |   | 11/1991 | Lind |         |
| 5,250,054 | A | * | 10/1993 | Li | 606/148 |
| 5,447,512 | A | * | 9/1995  | Wilson et al. | 606/139 |
| 5,454,827 | A |   | 10/1995 | Aust et al. |         |
| 5,514,076 | A |   | 5/1996  | Ley |         |
| 5,573,542 | A |   | 11/1996 | Stevens et al. |         |
| 5,618,294 | A |   | 4/1997  | Aust et al. |         |
| 5,709,692 | A | * | 1/1998  | Mollenauer et al. | 606/141 |
| 5,741,278 | A |   | 4/1998  | Stevens et al. |         |
| 5,807,241 | A | * | 9/1998  | Heimberger | 600/142 |
| 5,851,212 | A |   | 12/1998 | Zirps et al. |         |
| 5,885,288 | A |   | 3/1999  | Aust et al. |         |

(Continued)

OTHER PUBLICATIONS

ExpresSew™ Suter Passing System, Surgical Solutions, Inc., 2004.

(Continued)

*Primary Examiner* — Alexander Orkin
(74) *Attorney, Agent, or Firm* — Schwegman Lundberg & Woessner, P.A.

(57) ABSTRACT

A method for suturing soft tissue in arthroscopic or endoscopic procedures. The method includes inserting a bendable steerable arm in a straightened configuration through an incision, curving the steerable arm, piercing the tissue, deploying a suture holder from a bore of the steerable arm, moving the suture holder relative to the bendable steerable arm, and suturing the tissue.

11 Claims, 18 Drawing Sheets

(56) References Cited

U.S. PATENT DOCUMENTS

| | | | |
|---|---|---|---|
| 5,899,914 A | 5/1999 | Zirps et al. | |
| 5,919,199 A | 7/1999 | Mers Kelly et al. | |
| 5,938,678 A | 8/1999 | Zirps et al. | |
| 5,947,982 A | 9/1999 | Duran | |
| 5,972,005 A | 10/1999 | Stalker et al. | |
| 5,980,538 A * | 11/1999 | Fuchs et al. | 606/145 |
| 6,012,494 A * | 1/2000 | Balazs | 138/119 |
| 6,048,339 A | 4/2000 | Zirps et al. | |
| 6,053,907 A | 4/2000 | Zirps | |
| 6,062,951 A | 5/2000 | Zirps | |
| 6,077,287 A | 6/2000 | Taylor et al. | |
| 6,139,214 A | 10/2000 | Zirps et al. | |
| 6,171,316 B1 | 1/2001 | Kovac et al. | |
| 6,187,000 B1 | 2/2001 | Davison et al. | |
| 6,283,979 B1 | 9/2001 | Mers Kelly et al. | |
| 6,524,320 B2 | 2/2003 | DiPoto | |
| 6,530,889 B1 | 3/2003 | Konings et al. | |
| 6,554,832 B2 | 4/2003 | Shluzas | |
| 6,626,917 B1 * | 9/2003 | Craig | 606/144 |
| 6,645,218 B1 | 11/2003 | Cassidy et al. | |
| 6,652,553 B2 | 11/2003 | Davison et al. | |
| 6,743,239 B1 | 6/2004 | Kuehn et al. | |
| 6,755,843 B2 | 6/2004 | Chung et al. | |
| 2002/0147456 A1 * | 10/2002 | Diduch et al. | 606/144 |
| 2003/0036748 A1 * | 2/2003 | Cooper et al. | 606/1 |
| 2003/0065337 A1 | 4/2003 | Topper et al. | |
| 2003/0229271 A1 * | 12/2003 | Briscoe et al. | 600/229 |
| 2004/0010273 A1 * | 1/2004 | Diduch et al. | 606/144 |
| 2004/0030375 A1 * | 2/2004 | Pierce | 607/125 |
| 2004/0064136 A1 | 4/2004 | Papineau et al. | |
| 2004/0138525 A1 * | 7/2004 | Saadat et al. | 600/104 |
| 2004/0181242 A1 | 9/2004 | Stack et al. | |
| 2004/0199051 A1 | 10/2004 | Weisel | |
| 2004/0199184 A1 | 10/2004 | Topper et al. | |
| 2004/0225183 A1 * | 11/2004 | Michlitsch et al. | 600/106 |
| 2004/0249393 A1 * | 12/2004 | Weisel et al. | 606/144 |
| 2005/0065536 A1 | 3/2005 | Ewers et al. | |

OTHER PUBLICATIONS

Goose Neck® Snares and Microsnares, The Endovascular Company, 2004.

Innovative Solutions in Shoulder Reconstruction, Arthrotek™, Inc., 2002.

Innovative Solutions, Caspari™ Suture Punch System, Arthrotek®, Inc., 2002.

* cited by examiner

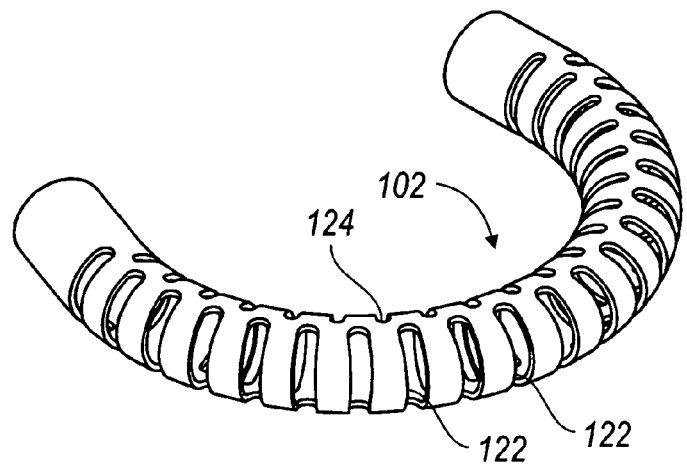
FIG. 8
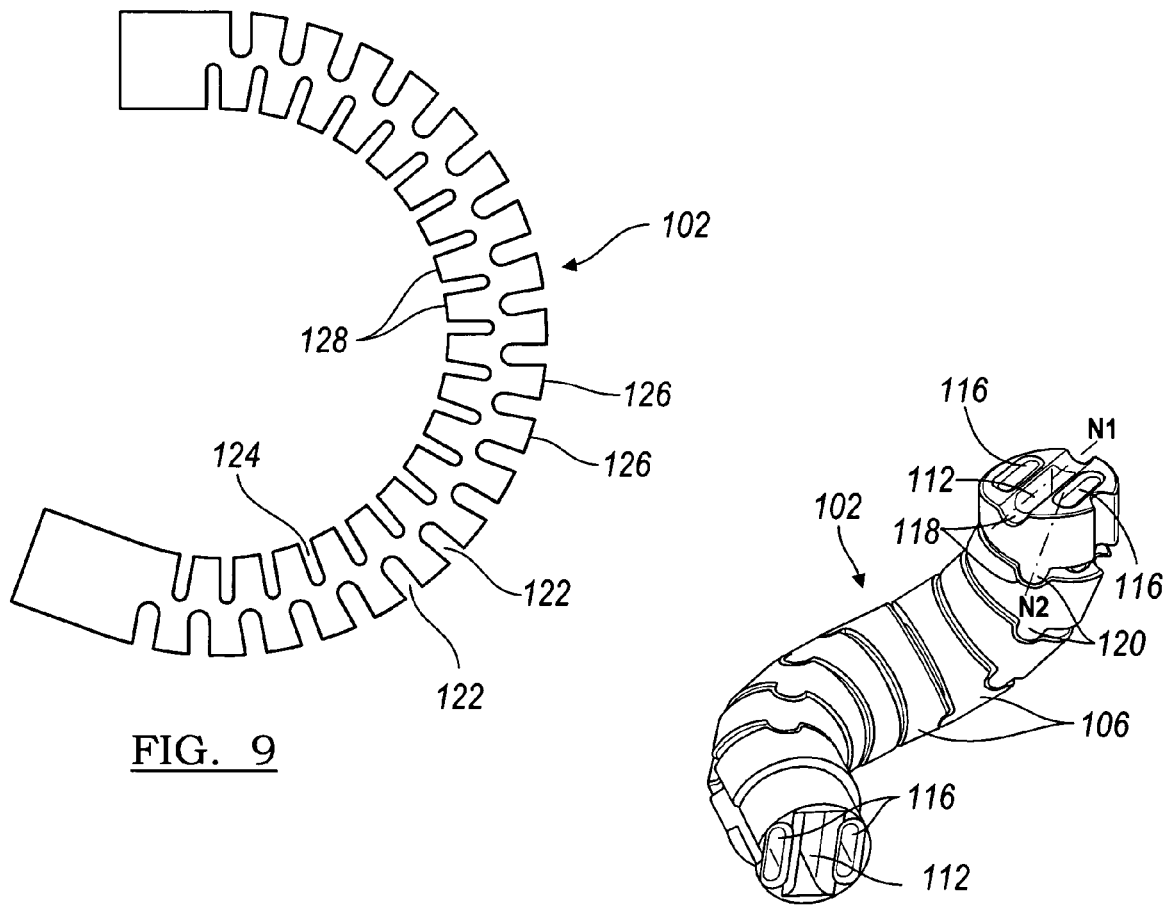
FIG. 9
FIG. 10

STEERABLE SUTURE PASSING DEVICE

CROSS-REFERENCE TO RELATED APPLICATIONS

This application claims the benefit of U.S. Provisional Application No. 60/707,238, filed on Aug. 11, 2005. The disclosure of the above application is incorporated herein by reference.

INTRODUCTION

Various devices and methods are known for suturing soft tissue in connection with arthroscopic, endoscopic or other surgical procedures. These and other small-incision or less invasive surgical procedures require that suturing and the associated manipulation of suturing needles, suture passers, retrievers, or other suture instruments are performed in confined and not-easily accessible areas.

Although the existing devices can be satisfactory for their intended purposes, there is still a need for procedures and devices that provide greater flexibility and maneuverability for suturing in ordinary and less invasive procedures.

SUMMARY

The present teachings provide a method for suturing soft tissue in arthroscopic or endoscopic procedures. The method includes inserting a bendable steerable arm in a straightened configuration through an incision, curving the steerable arm, piercing the tissue, deploying a suture holder from a bore of the steerable arm, moving the suture holder relative to the bendable steerable arm, and suturing the tissue.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 8 is a perspective view of a steerable arm according to the present teachings;

FIG. 9 is a side view of a steerable arm according to the present teachings;

FIG. 10 is a perspective view of a steerable arm according to the present teachings, the arm shown flexed in a three-dimensional curved configuration;

DETAILED DESCRIPTION

The following description is merely exemplary in nature and is in no way intended to limit the invention, its application, or uses. The present teachings can be used for any arthroscopic, endoscopic or other procedures in which suturing or manipulating of soft tissue is required.

Figure 1:
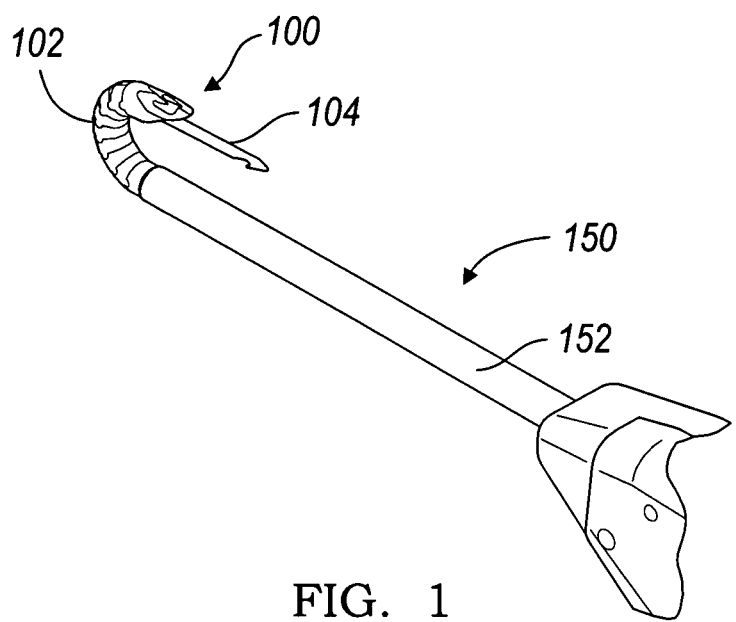
FIG. 1 is a perspective view of a suture-passing device according to the present teachings.
Figure 2:
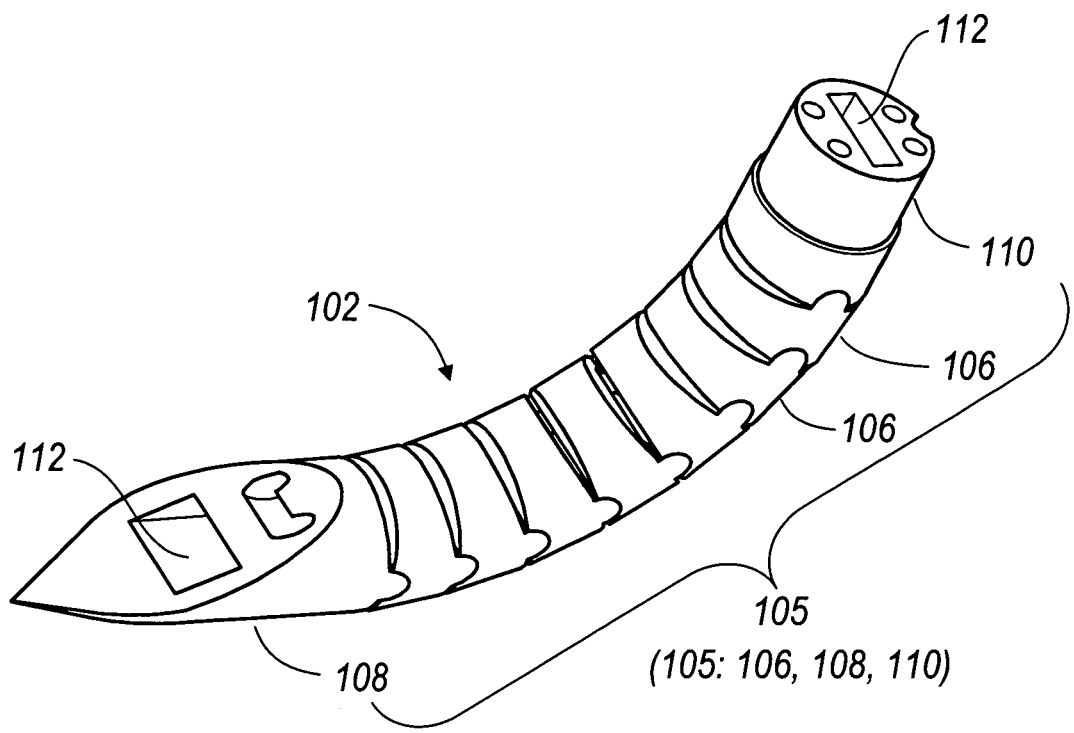
FIG. 2 is a perspective view of a steerable arm according to the present teachings.
Figure 3A:
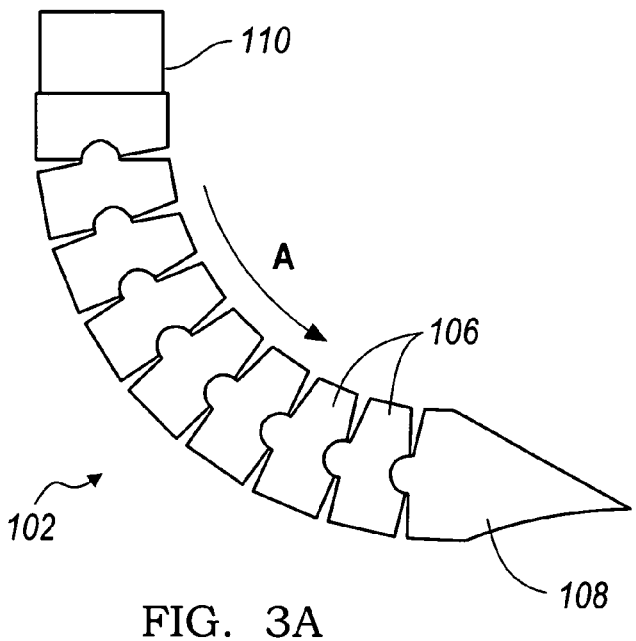
FIG. 3A is a side view of the bendable steerable arm of FIG. 2, shown in a flexed configuration.
Figure 3B:
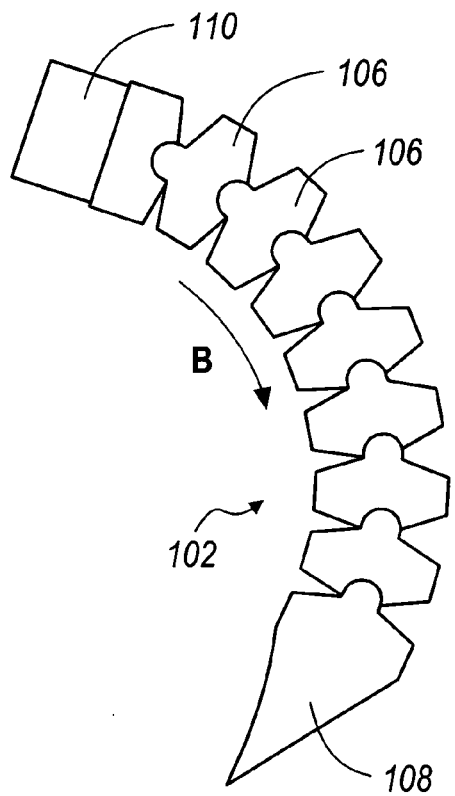
FIG. 3B is a side view of a steerable arm according to the present teachings shown in a flexed configuration.
Figure 4:
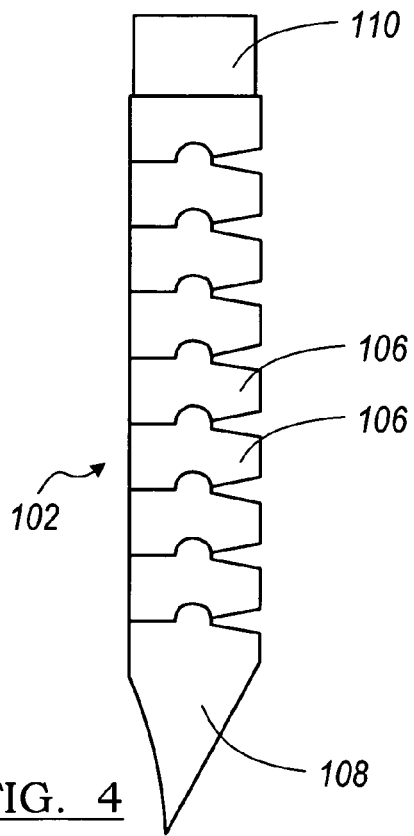
FIG. 4 is a side view of the bendable steerable arm of FIG. 2, shown in a straightened configuration.
Figure 5:
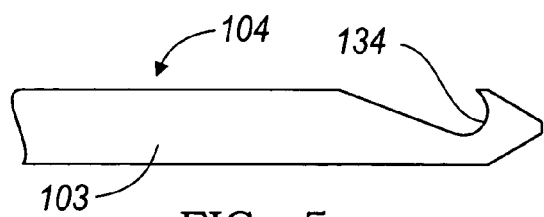
FIG. 5 is a side view of a suture holder according to the present teachings.
Figure 6:
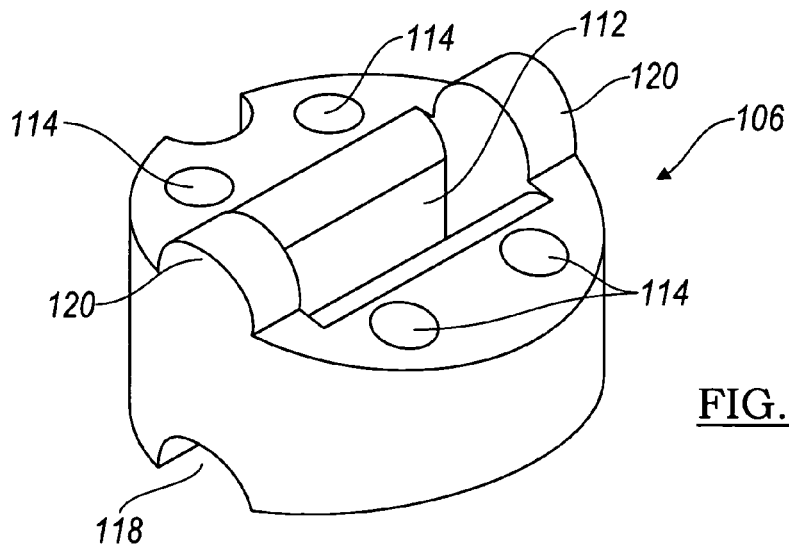
FIGS. 6 and 7 are top and bottom perspective views of intermediate link elements of a steerable arm according to the present teachings.

Referring to FIG. 1, an exemplary suture-passing device 100 according to the present teachings includes a bendable steerable arm 102, and a suture holder 104 that can retrieve, pull or push suture or soft tissue. The bendable steerable arm 102 can be articulatably made from interlocking discrete elements as illustrated in FIG. 2, or can be made integrally from a superelastic tube, such as a nitinol tube, as illustrated in FIG. 8, or from any other bendable steerable construct. The suture-passing device 100 can be mounted on a shaft 152 of an actuating handle 150 and actuated by various actuators, which operate to manipulate the bendable steerable arm 102, the suture holder 104, and the suture, as discussed below in further detail. For example, the bendable steerable arm 102 can be flexed by one of the actuators to attain various two-or three-dimensional curved configurations for piercing or otherwise accessing tissue, as discussed below. The shaft 152 can be tubular and substantially rigid and straight, although a rigid curved shaft 152 can also be used. The shaft 152 can also be used directly to manipulate the configuration of the bendable steerable arm 102.

Figure 11A:
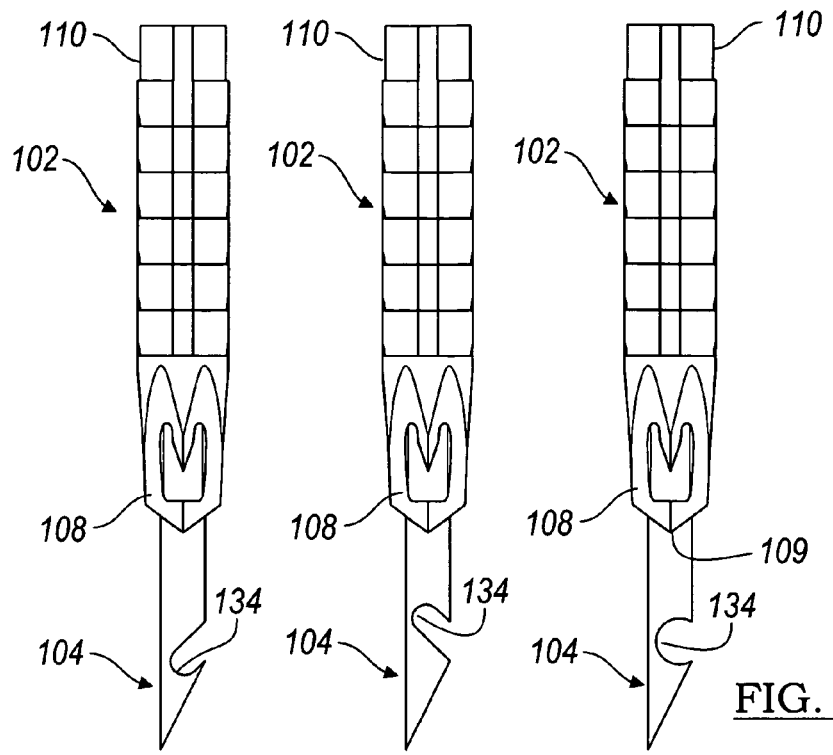
FIGS. 11A-11L are plan views of different suture holders loaded on steerable arms according to the present teachings.
Figure 12A:
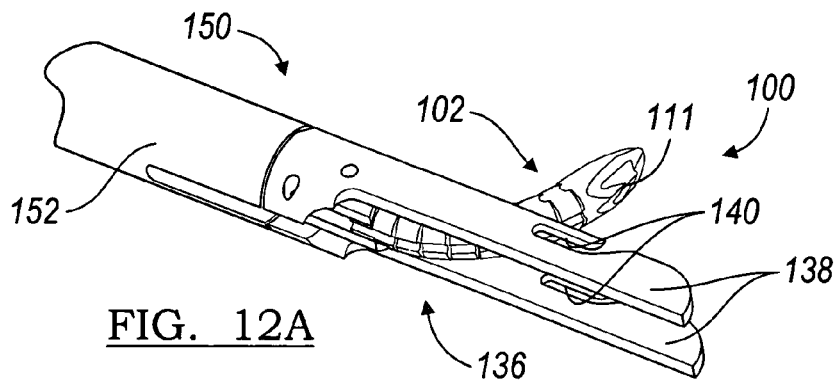
FIG. 12A is a perspective view of a steerable arm with a jaw shown in a closed position according to the present teachings.

Referring to FIGS. 2-4, 6, 7, 10 and 11A, the bendable steerable arm 102 can be cannulated and can include a plurality of link elements 105, which include intermediate link elements 106, a coupling end element 110 connectable to the shaft 152, and a tip element 108 configured for piercing soft tissue and deploying the suture holder 104. The tip element 108 can include, for example, a tissue piercing portion 109, as shown in FIG. 11A, and a suture-holding portion 111, as illustrated in FIG. 12A, for holding suture directly, and not through the suture holder 104, if so desired. A bore or slot 112 that can be central or offset and pass through all of the link elements 105 defines the cannula of the bendable steerable arm 102. Other openings 114 or slots 116 of various shapes can be used as passages for actuator cables, rods, wires, shafts, or other actuator devices 211 (shown in FIG. 16) for steering the bendable steerable arm 102, and/or manipulating the suture holder 104. For example, four actuating cables 211 can be passed through the four openings 114 and attached to actuator mechanisms on the handle 150, such that retracting and reducing the length of a first cable causes the bendable steerable arm 102 to bend in a first direction, for example in the direction shown in FIG. 3A by curved arrow A, and retracting a second cable causes the bendable steerable arm 102 to bend in the second direction opposite to the first direction, illustrated in FIG. 3B by curved arrow B, when the intermediate link elements 106 are doubly wedged, as shown in FIG. 3B, rather than singly wedged, as shown in FIG. 3A. Similarly, third and second fourth actuating cables 211 can be used to bend the bendable steerable arm 102 in directions similar to directions A and B, but in a plane that is orthogonal to the plane illustrated in FIGS. 3A and 3B. Instead of four separate actuating cables 211, two pairs of continuous actuating cables 211 can be used, one pair for bending in each of two orthogonal bending planes. Referring to FIG. 10, two pairs of flat ribbons passing through the pairs of elongated slots 116 can also be used for bending the bendable steerable arm 102 in two orthogonal or otherwise angled planes.

Referring to FIGS. 3A, 3B, 4, 6 and 7, the intermediate link elements 106 can be singly, doubly or multiple wedge-shaped and include conforming grooves 118 and projections 120 on opposite faces configured to allow relative articulation between adjacent link elements 105, including pivoting and multi-axial rotation, to provide bending in two orthogonal planes and twisting motion, as illustrated in FIG. 10. The grooves 118 and projections 120 can be semi-cylindrical for pivoting about an axis or semi-spherical for multi-axial articulation.

Referring to FIG. 10, the link elements 106 can be configured for relative movement that allows the bendable steerable arm 102 to be selectively twisted and bent or flexed in three-dimensional curved configurations, Twisting, corkscrew or spiral motion can be achieved by manipulating the rigid shaft 152, although bending/flexing motion can also be confined to planar or two-dimensional curved configurations, if so desired, by providing known actuators configured for planar actuation in one or two orthogonal planes as discussed above.

Figure 7:
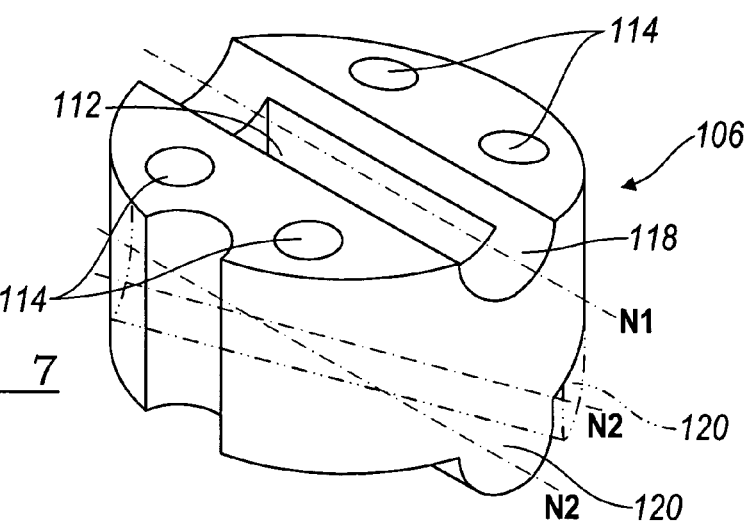
Figure 7A:
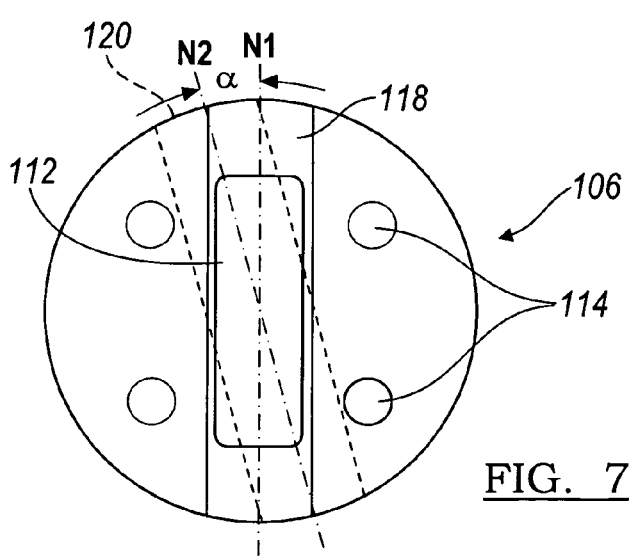
FIG. 7A is a plan view of the intermediate link element of FIG. 7.

The corkscrew motion of FIG. 10 can be easily enabled by modifications of the relative orientation of axes N1 and N2 of the grooves 119 and projections 120 of the link elements 106, respectively. In the exemplary illustration of FIGS. 7 and 7A, the groove 118 and the corresponding projection 120 are shown as substantially parallel, along axes N1 and N2 respectively. Such alignment enables two-dimensional bending or flexing. The axes N1 and N2 can also be oriented such that they define an angle α, as shown in phantom lines in FIGS. 7 and 7A. Specifically, the groove 118 and the projection 120 can be displaced in the circumferential direction by the angle α, thereby enabling three-dimensional flexing of the steerable arm 102, as shown in FIG. 10. The value of the angle α can be selected for allowing a particular shape of corkscrew type of motion. Typical values for the angle α can be, for example, 15-40 degrees, or any other value desired.

Referring to FIGS. 8 and 9, the bendable steerable arm 102 can be made as a monolithic cannulated tube with pluralities of staggered cut-outs 122, 124 that define corresponding pluralities of wedge-shaped staggered link elements 126, 128 that combine to impart flexibility and steerability to the monolithic sterable arm 102, such that the steerable arm can be manipulated in two-or three-dimensional curved configurations. Two dimensional configurations include planar bending. Three dimensional configurations include various types of curving, including twisting with or without planar bending, and/or corckscrew curving. The staggered cut-outs 122, 124 and the corresponding wedged link element 126, 128 provide sufficient flexibility and freedom of motion to achieve bending of the monolithic steerable arm 102 in two orthogonal or otherwise angled planes, as well as twisting or spiral motion similar to that illustrated in FIG. 10 for modularly connected link elements 106. It will be appreciated that other cut-out and link element configurations and shapes can be used for steerability. Further, the bendable steerable arm 102 can be made from nitinol that can be trained to a particular curved configuration, or can be used untrained.

Figure 11B:
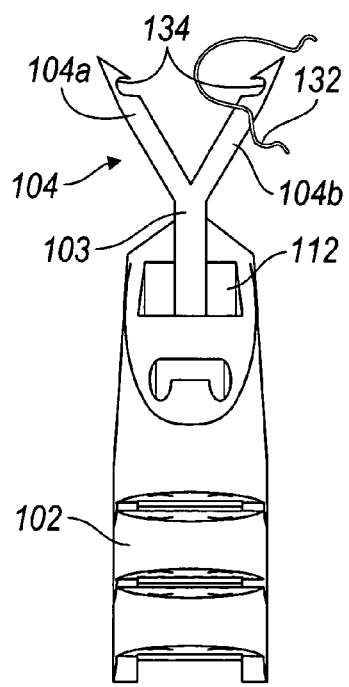
Figure 11C:
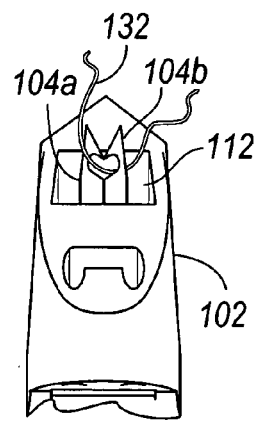
Figure 11D:
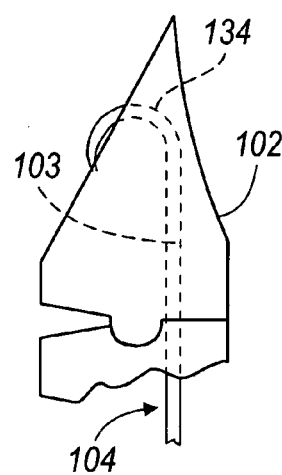
Figure 11E:
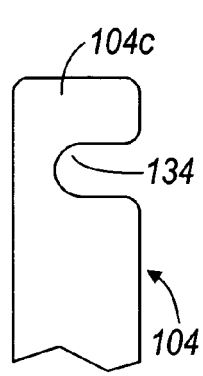
Figure 11F:
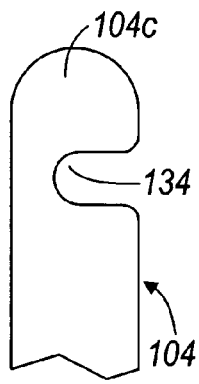
Figure 11G:
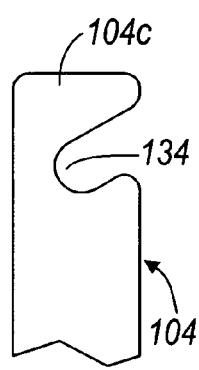
Figure 11H:
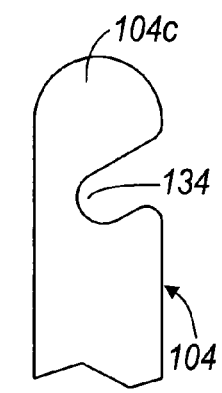
Figure 11I:
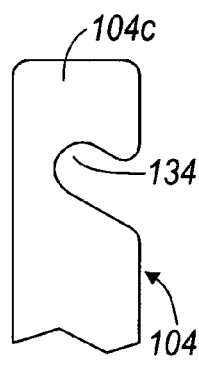
Figure 11J:
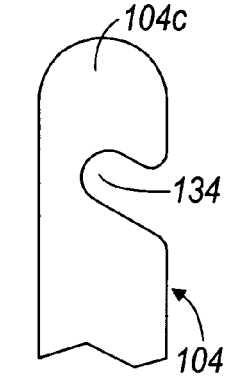
Figures 11K, 11L:
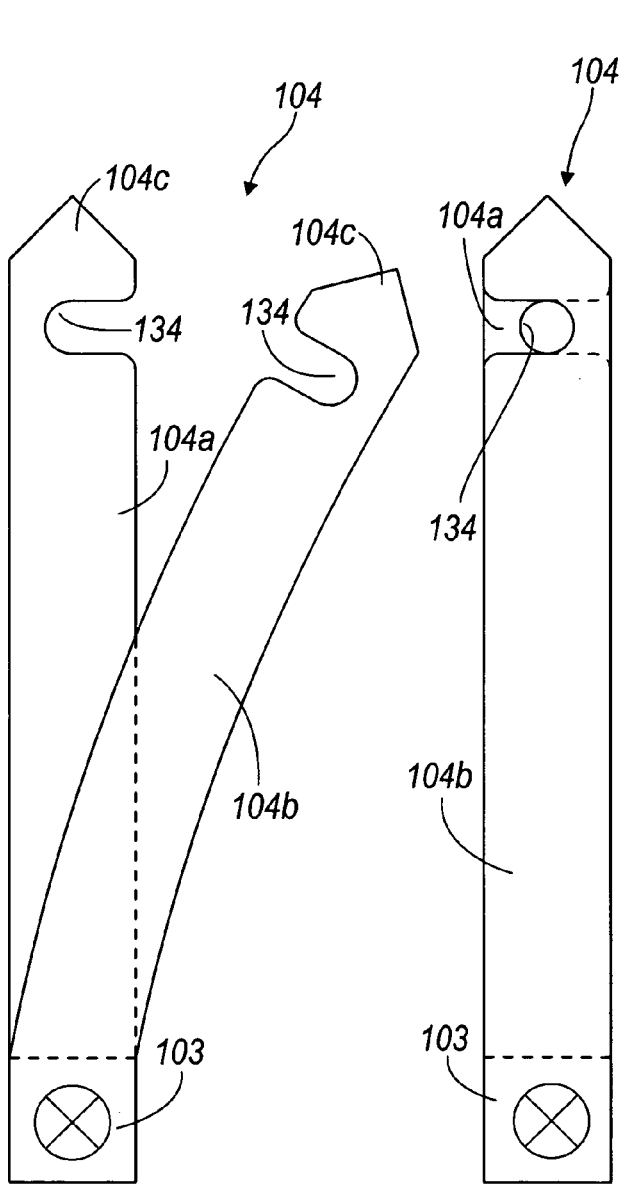

Referring to FIGS. 5 and 11A-11L, the suture holder 104 can include a shaft 103 and can be flat or ribbon-like, as illustrated in FIG. 11A or wire-like with a curved hook end, as illustrated in FIG. 11D. Referring to FIGS. 11B and 11C, the suture holder 104 can have split or bifurcated arms 104a, 104b extending from the shaft 103, which can trap a suture 132 when retracted into the bendable steerable arm 102. In another aspect, double arms 104a, 104b of width equal to the width of the stem 103 can be used. The double arms 104a, 104b can be welded or otherwise fastened at their proximal ends to the stem in overlapping fashion, as shown in FIGS. 11K and 11L, in open and closed configurations respectively. The suture holder 104 can include an eye, notch, hook or other engagement feature 134 for engaging the suture 132. The engagement feature 134 can have different shapes orientations, as illustrated in FIGS. 11A and 11E-11J. The suture holder 104 can have a distal tip 104c, which can be sharp or pointed, as shown in FIG. 11A, or flat, as shown in FIGS. 11E, 11G, and 11I, or curved as shown in FIGS. 11F, 11H and 11J. The suture holder 104 can be made of biocompatible material including stainless steel or a superelastic material, such as nitinol. Different suture holders 104 can be provided with the suture-passing device 100 to be selectively used with the bendable steerable arm 102 at the discretion of the surgeon. The suture holder 104 can be slidably inserted in the bore 112 of the bendable steerable arm 102. The suture holder 104 can be connected to an actuator, as described below, such that the suture holder 104 can be selectively extended out of and retracted into the bore 112 of the bendable steerable arm 102, whether the bendable steerable arm 102 is in a straight or curled/deformed position. The suture holder 104 can be disposable.

Figure 12B:
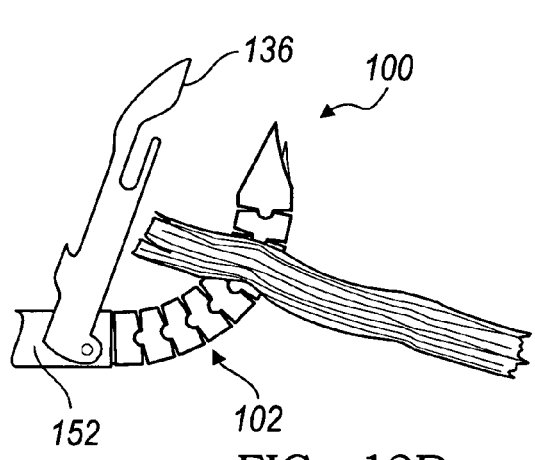
FIG. 12B is a side view of a steerable arm with a jaw shown in an open position according to the present teachings.

Referring to FIGS. 12A-12E, the bendable steerable arm 102 can be provided with a movable jaw 136. The jaw 136 can be pivotably coupled to the shaft 152 of the handle 150 or other portion of the handle 150, such that the jaw 136 can be moved between a closed position substantially coextensive to the shaft 152, or to the straight configuration of the bendable steerable arm 102, as shown in FIG. 12A, and an open position at an angle to the shaft 152, or to the straight configuration of the bendable steerable arm 102, as shown in FIG. 12B.

Figure 12C:
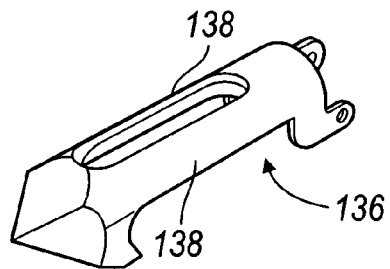
FIG. 12C is a perspective view of a jaw according to the present teachings.
Figure 12D:
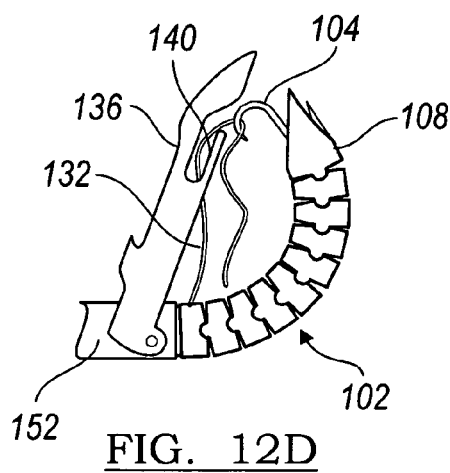
FIG. 12D is a side view of a steerable arm with a jaw shown in an open position and holding a suture according to the present teachings.
Figure 12E:
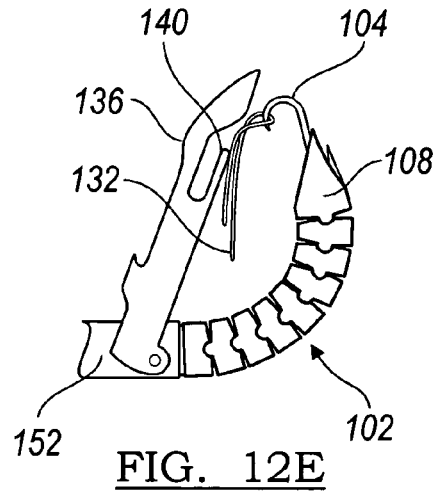
FIG. 12E is a side view of a steerable arm with a jaw shown in an open position for retrieving suture from a suture holder according to the present teachings.

The jaw 136 can include a single or double prong 138 and a suture engagement hook 140. The double prong 138 can be open-looped, as shown in FIG. 12A, or closed-looped, as shown in FIG. 12C. The jaw 136 can be used to retain suture 132 on the suture engagement hook 140 to be retrieved by the suture holder 104, which is appropriately oriented by the bendable steerable arm 102, as illustrated in FIG. 12D. Conversely, the suture engagement hook 140 of the jaw 136 can be used to retrieve suture 132 from the deployed suture holder 104, as illustrated in FIG. 12E. The jaw 136, in association with the bendable steerable arm 102, can also be used as a soft tissue clamp, for grasping and retaining tissue, as illustrated in FIG. 12B. Any actuator known in the art can be used to move the jaw 136 between the open and closed positions. The suture-passing device 100 can be used to access a joint or other body lumen through an incision in a compact configuration in which the jaw 136 is closed and the bendable steerable arm 102 is straight.

Figure 13:
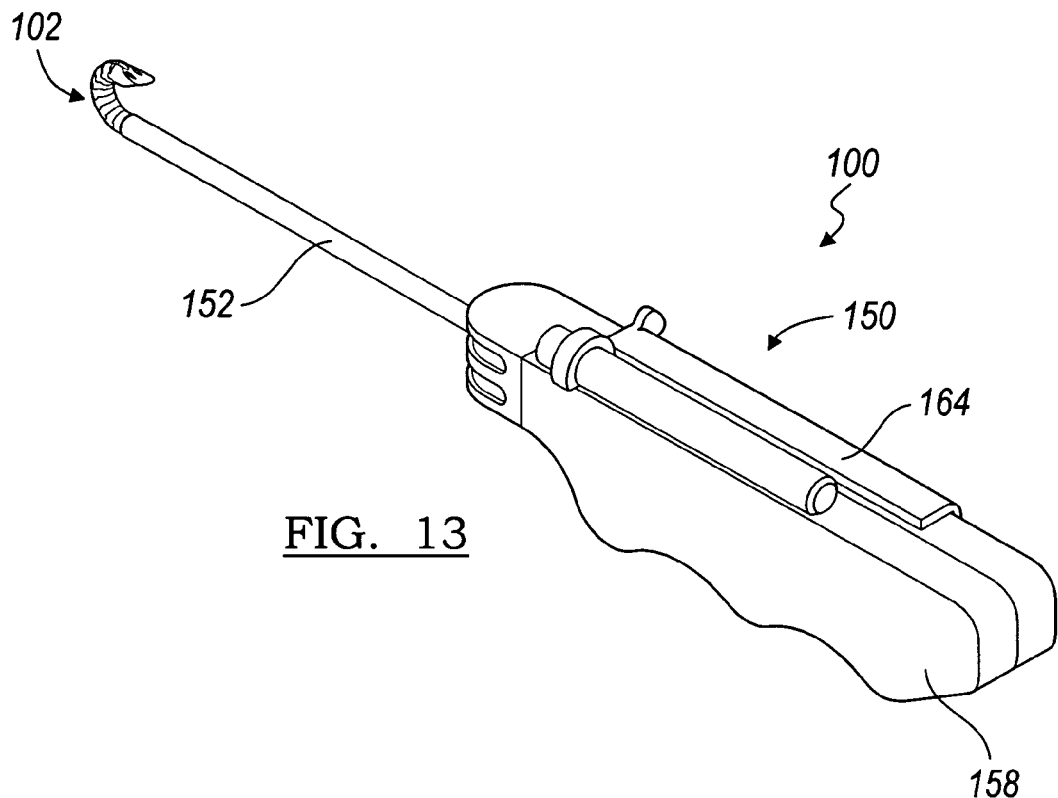
FIG. 13 is a perspective view of a suture-passing device with an axial handle according to the present teachings.
Figure 14:
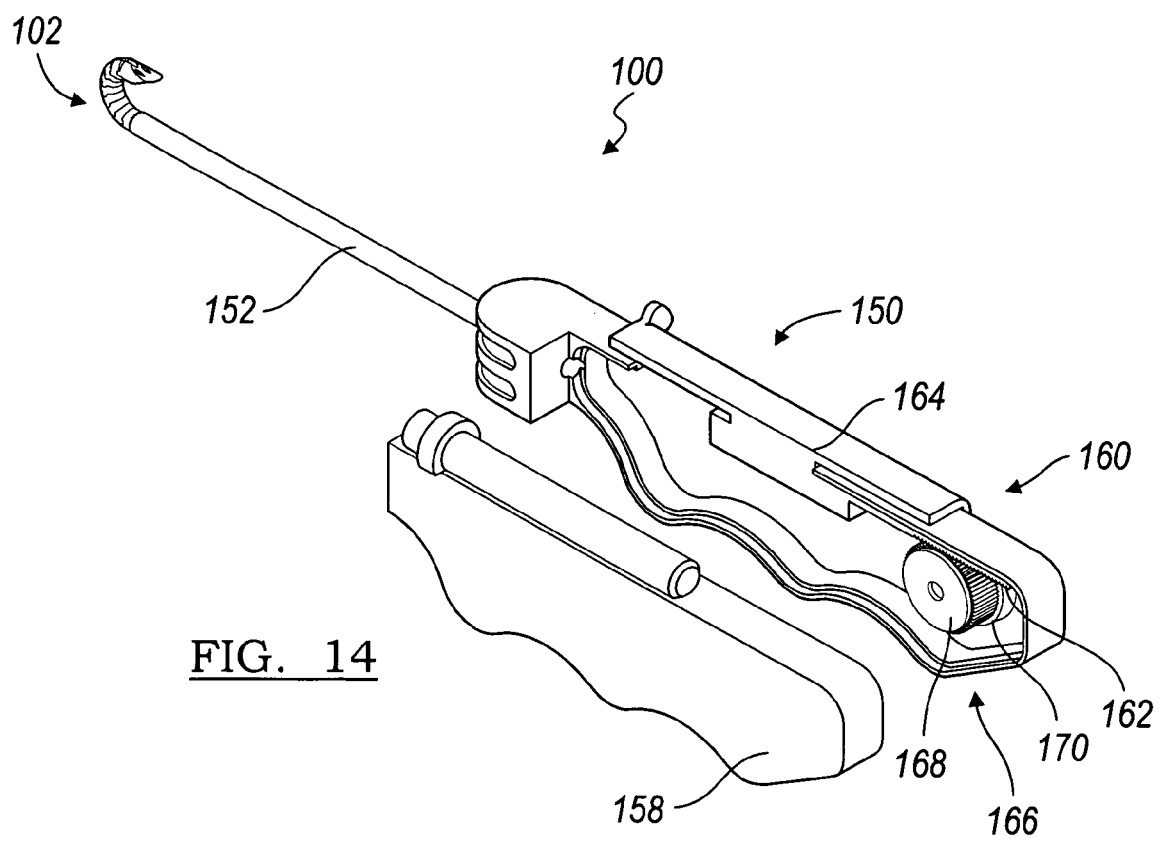
FIG. 14 is a partially exploded view of the suture passing device of FIG. 13.

Referring to FIGS. 13-18, the suture-passing device 100 can be coupled to an actuating or actuator-equipped handle 150, which can be configured with various actuation options depending on the application. In one exemplary aspect illustrated in FIGS. 13 and 14, the suture-passing device 100 can include an axial-type handle 150 having an ergonomic handle portion 158. The suture-passing device 100 illustrated in FIG. 13 can be used effectively and efficiently used in various repair procedures, such as, for example, procedures for superior labrum anterior-posterior (SLAP) lesions or other glenoid labrum lesions. The entire suture-passing device 100 or parts thereof can be disposable or replaceable or reusable. First and second actuators 160 can be used for steering, bending or flexing the bendable steerable arm 102, and for deploying the suture holder 104. One of the actuators 160 can be, for example, of the ratchet-type, as illustrated in FIG. 14.

Figure 15:
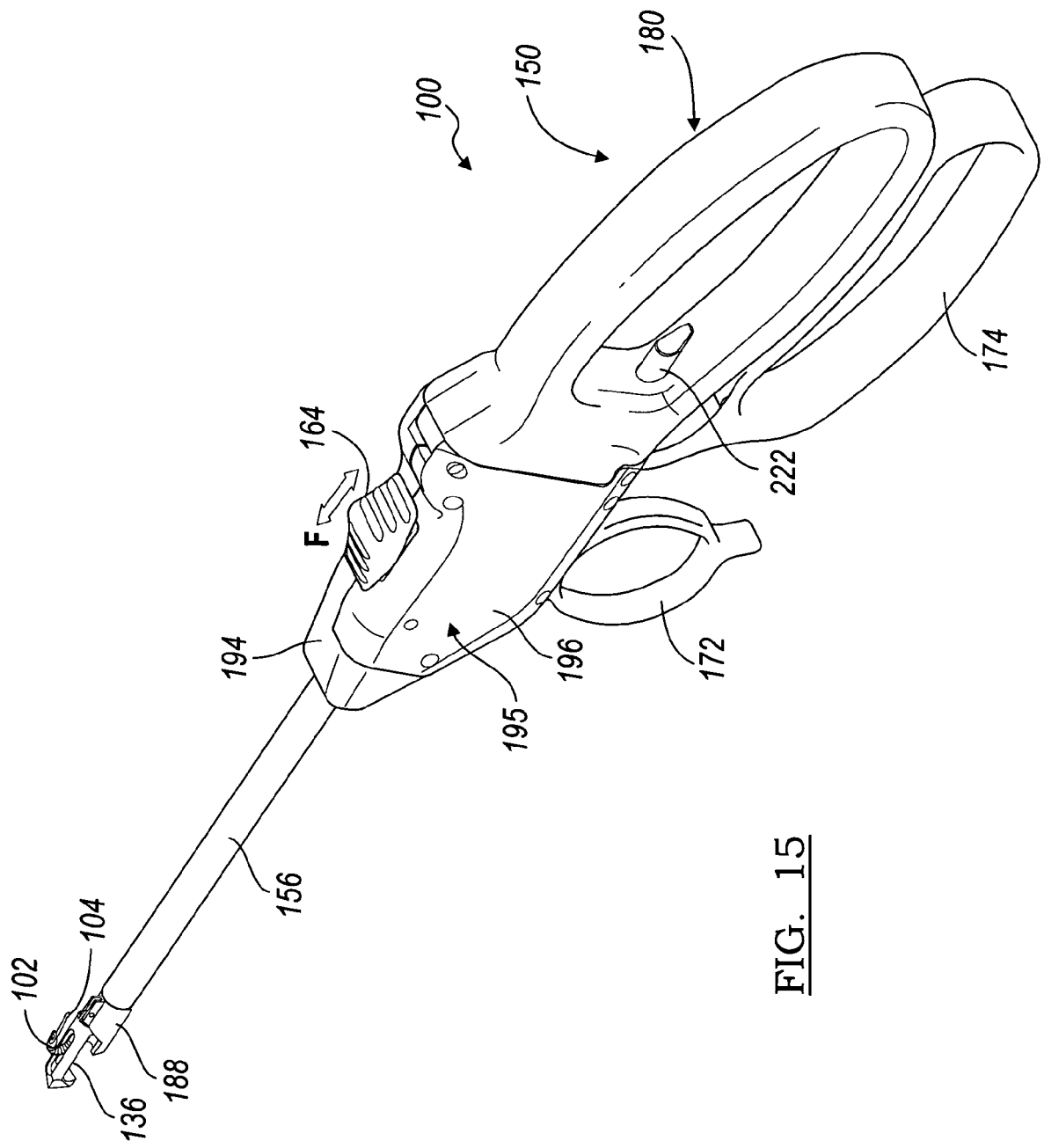
FIG. 15 is a perspective view of a suture-passing device according to the present teachings.

Referring to FIGS. 14 and 15, for the ratchet-type actuator 160, a straight ratchet or rack 162 operable by a slider 164 can be used to engage and rotate a roller or pinion 166. The roller 166 can include two unequal diameter spools 168, 170, over which cables, wires or ribbons guided through the openings 114 or slots 116 can be spooled for bending/flexing the bendable steerable arm 102 in a plane. The differential diameters of the spools 168, 170 can be adapted to accommodate the difference in radius of curvature of the convex and concave surfaces of the bendable steerable arm 102 in the flexed configuration.

With continued reference to FIGS. 13 and 14, the suture holder 104 can be actuated with another actuator 160 (not specifically shown) that is connected to the end of the suture holder 104 and passes through the tubular shaft 152 or other similar shaft. The suture-holder actuator 160 can be, for example, a substantially rigid elongated element, or a flexible cable, wire or ribbon, and can be operated by a trigger on the handle 150. The bendable steerable arm 102 can be configured in desired three-dimensional flexed and/or twisted configurations, such as shown in FIG. 10, by manipulating the shaft 152 using the handle 150, while providing some contact resistance at a portion of the bendable steerable arm 102.

Referring to FIGS. 15-18, an exemplary illustration of the suture-passing device 100 equipped with the jaw 136 is shown coupled with a handle 150 that has a pistol-like grip 180. The suture-passing device 100 illustrated in FIG. 15 can be used efficiently and effectively in various repair procedures, including rotator cuff repair procedures, for example. In addition to actuators for steering the bendable steerable arm 102 and deploying the suture holder 104, such as the actuators 160 described above in connection with FIGS. 13 and 14, for example, a third actuator can be used to operate the jaw 136. For example, a slider 164 can be manually operated to actuate the bendable steerable arm 102; a finger trigger 172 can be pulled to actuate the suture holder 104, and a lever 174 can be pulled toward the handle grip 180 to actuate the jaw 136.

Referring to FIGS. 15-18, the suture passing device 100 can include a removable and/or disposable cartridge 178 that cooperates with the slider 164 to actuate the bendable steerable arm 102. The pistol-grip handle 150 can be reusable. The slider 164 operates a cam gear 182 which engages a cam 184 in the cartridge 178. When the slider 164 is moved in the forward direction of an arrow "F", the cam 184 rotates in the direction of curved arrow "J2" and tightens the actuator cables/wires 211 that pass through the openings 114 of the bendable steerable arm 102, causing the bendable steerable arm 102 to cur in the direction of arrow "J3". Conversely, moving the slider 164 in the opposite direction operates to release the tension of the actuator wires and allows the bendable steerable arm 102 to straighten out.

Figure 17A:
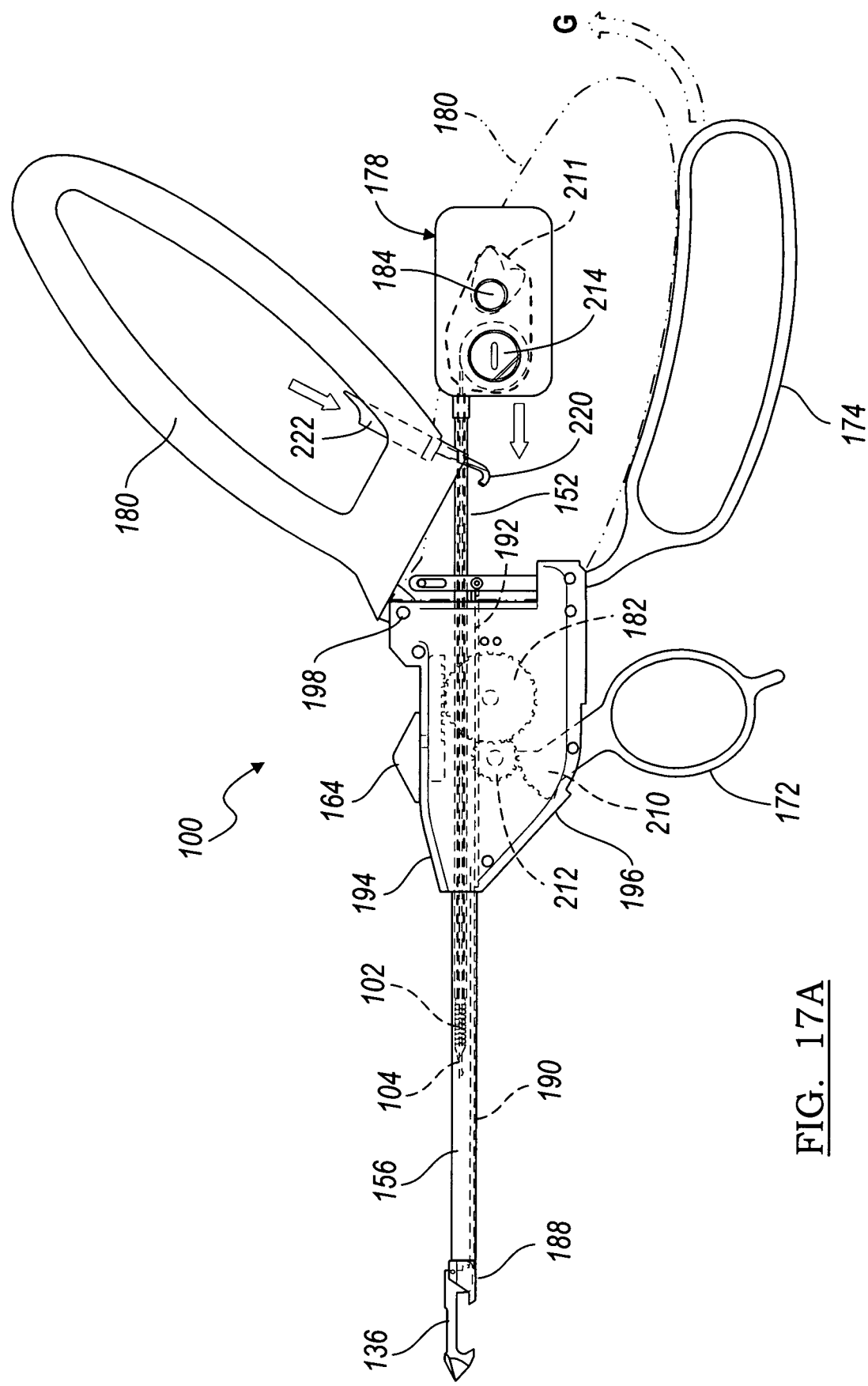
FIGS. 17A-17D are partially exploded side views illustrating athe operation of the suture-passing device of FIG. 15.
Figure 17B:
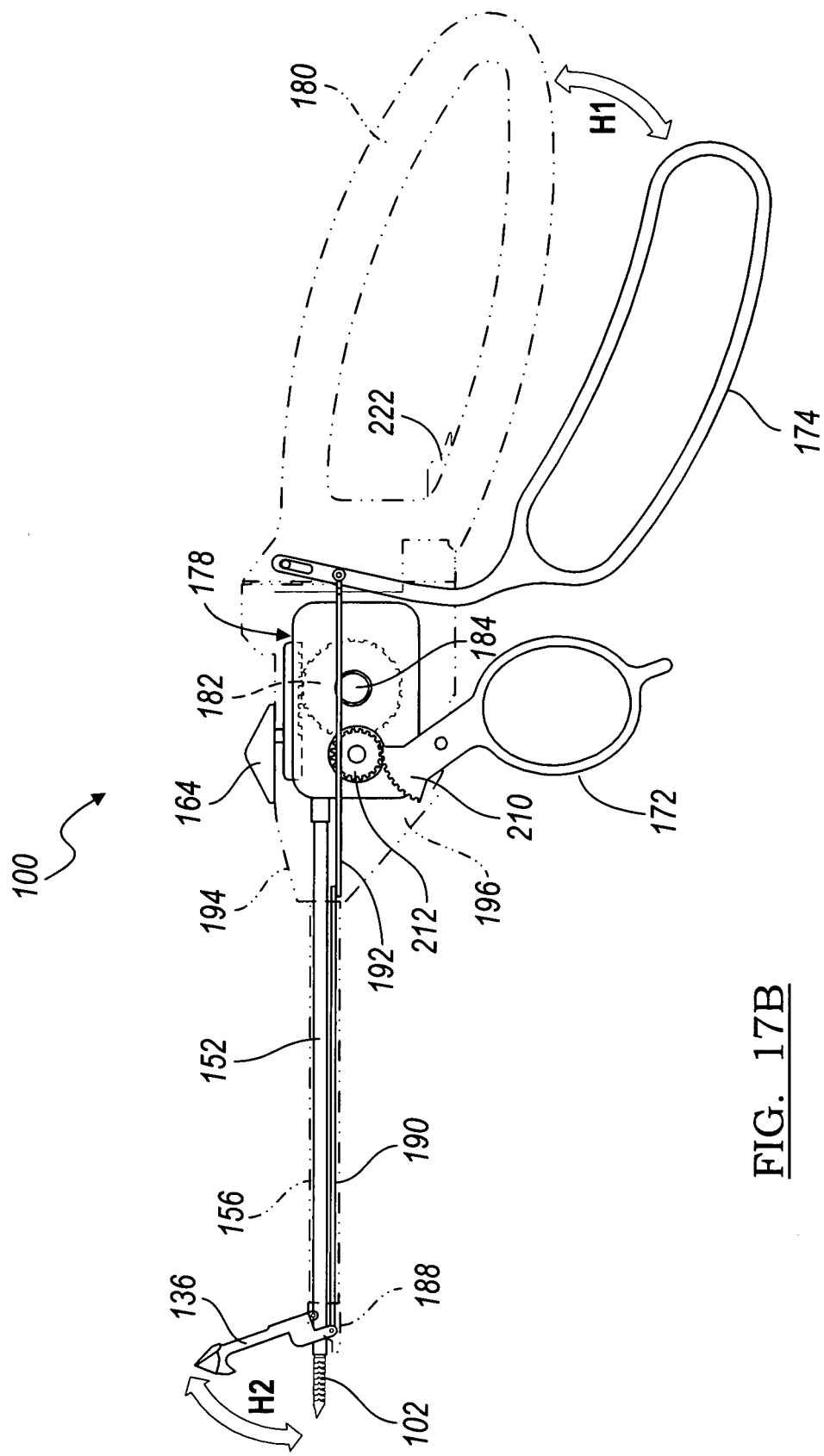

Referring to FIG. 17B, in an exemplary aspect the jaw 136 can be pivoted in the direction of arrow "H2" from a closed to an open position relative to a tray 188 by pressing the lever 174, which is operably connected with the jaw 136 for pivoting the jaw 136 with a substantially rigid rod 190 passing through a substantially rigid tube 156, which is coupled to the tray 188. The rod 190 can be coupled to a U-shaped actuator bar 192. The actuator bar 192 can be coupled to the lever 174 with a pin or dowel such that when the lever 174 is pulled closer to the handle grip 180 along an arrow "H1" the jaw 136 moves in the closed position. Conversely, when the lever 174 is released, the jaw 136 is moved to the open position. The lever 174 can be mounted with a dowel 198 on first and second housing covers 194, 196 that define a housing 195 for the cartridge 178.

Figure 17C:
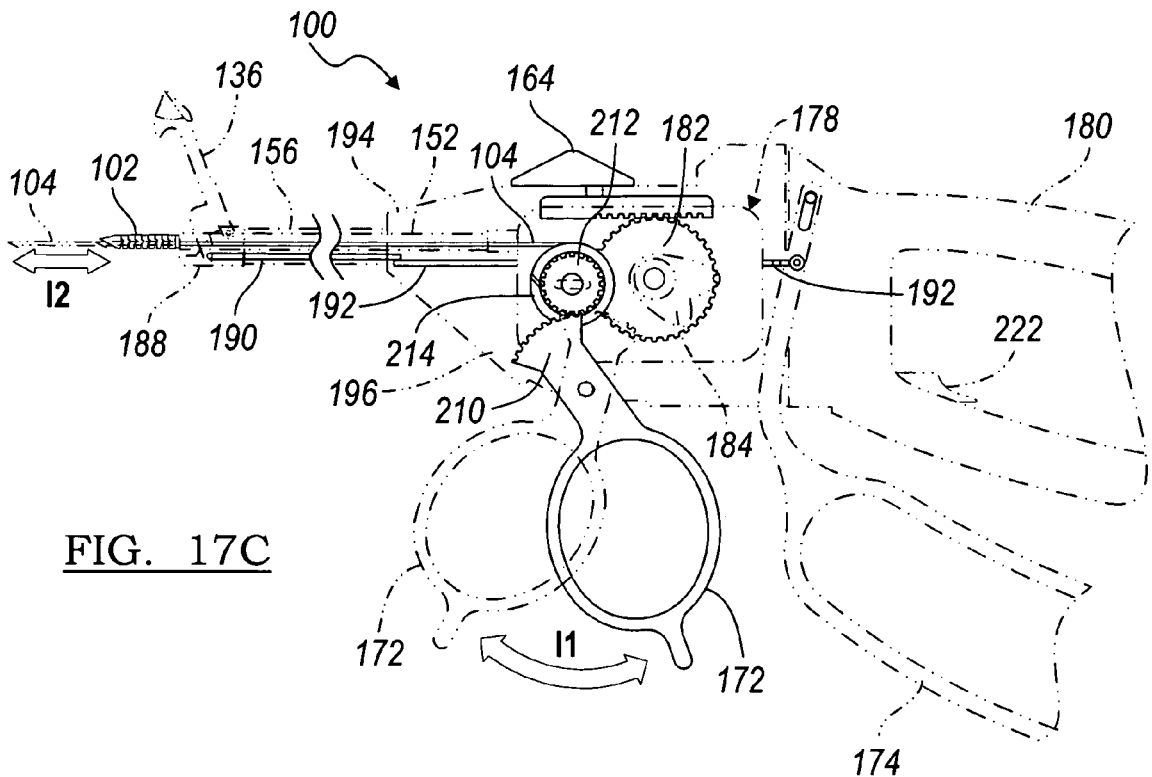
Figure 17D:
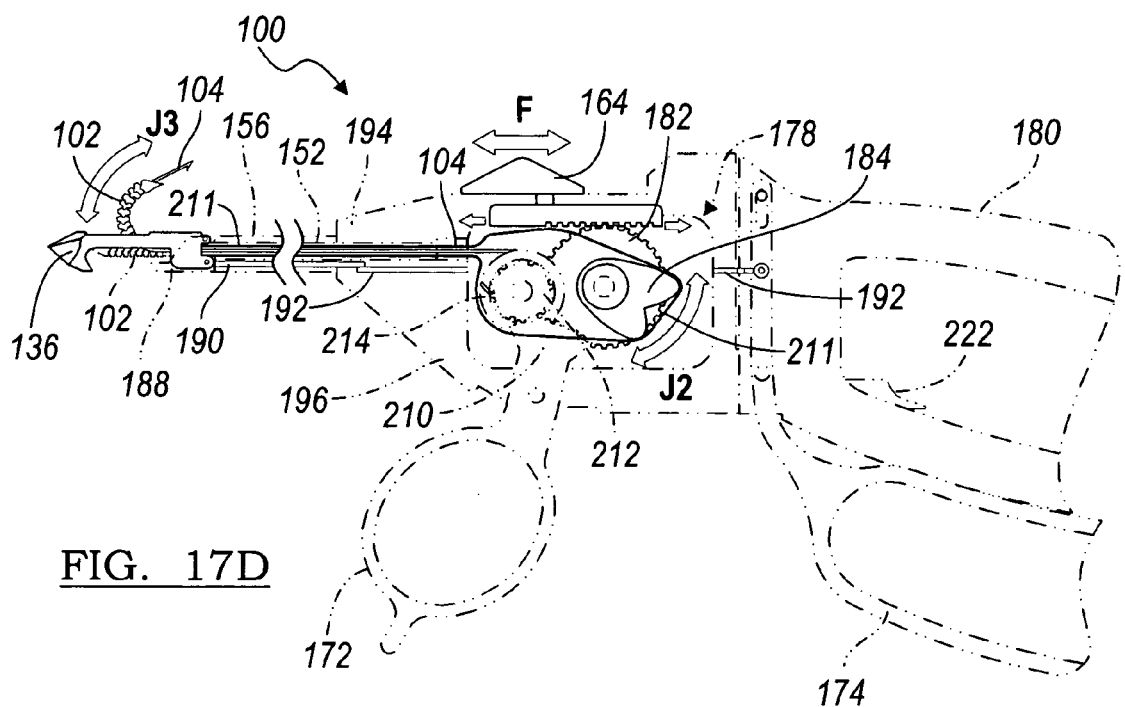
Figure 18:
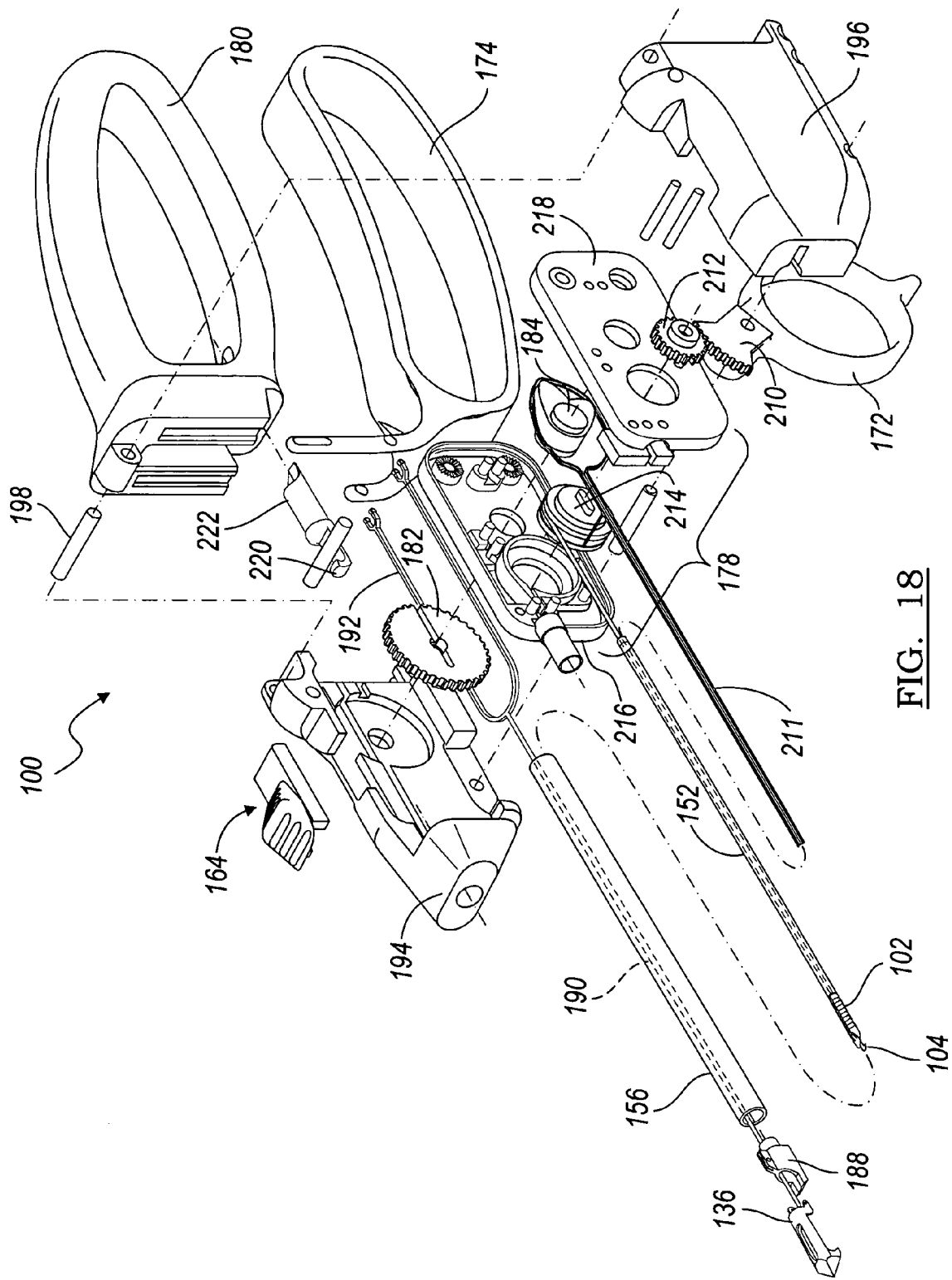
FIG. 18 is partially exploded views of the suture-passing device of FIG. 15.

Referring to FIG. 17C, the finger trigger 172 can be coupled to a partial gear 210 which can engage a spool gear 212 mounted on the second housing cover 196. A spool 214 housed in the cartridge 178 can engage the spool gear 212. The wire shaft 103 of the suture holder 104 can be wrapped around the spool 214. When the trigger 172 is pushed away from the handle grip 180 along a direction "I1", rotational motion is transmitted through partial gear 210 and spool gear 212 to the spool 214, causing the wire shaft 103 to be unwrapped from the spool 214 and the suture holder 104 to extend out of the bore 112 of the bendable steerable arm 102 along the forward direction of double arrow "I2". Pulling the finger trigger 172 toward the handle grip 180, causes the spool 210 to rotate in the opposite direction, thereby retracting the suture holder 104 through the bore 112 in its storage position.

Figure 16:
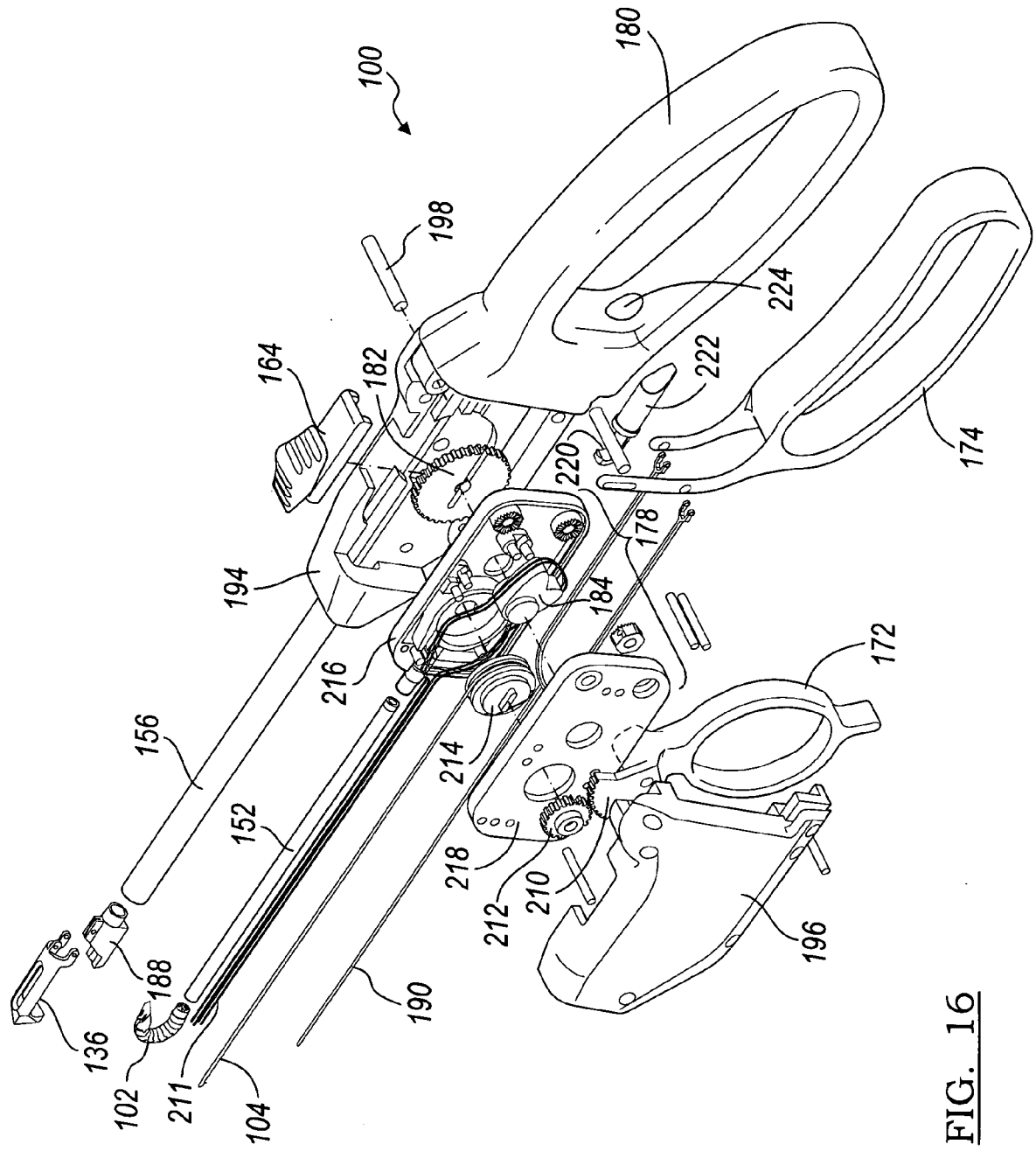
FIG. 16 is partially exploded views of the suture-passing device of FIG. 15.

Referring to FIGS. 16 and 17A, the cartridge 178 can include a cartridge base 216 and a cartridge cover 218. The cartridge 178 can house the cam 184 and the spool 214, with at least a portion of the shaft 103 of the suture holder 104 loaded on the spool 214. The cartridge can also include the steerable arm 102 through which the suture holder 104 is deployed when the cartridge is operationally loaded on the suture-passing device 100. The cartridge 178 can be loaded in the rear of the housing 195 of the suture passing-device 100 after unlocking the handle grip 180 and allowing the handle grip 180 to rotate upwards about the dowel 198 in a direction indicated by arrow "G". In its locked position, the handle grip 180 can be secured against rotation by a latch 220 that engages a dowel coupled to the housing 195. The latch 220 is also coupled to a release button 222 that is accessible through an opening 224 in the handle grip 180, such that pushing the release button 222 releases the handle grip 180 from its locked position and allows rotation of the handle grip 180 for inserting or removing the cartridge 178.

Although particular actuators have been described for particular functions, it will be appreciated that any combination of the actuators described or other known actuators can be used for actuating the jaw 136, the bendable steerable arm 102 and the suture holder 104.

Figure 19A:
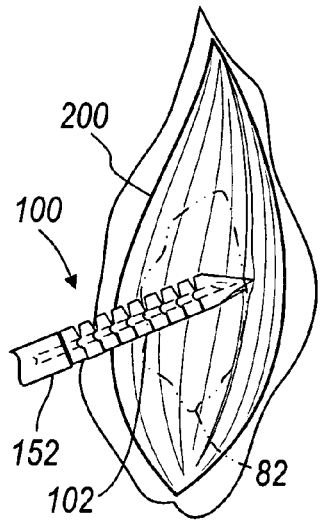
FIGS. 19A-19F are environmental views of the suture passing device shown in various stages in operation according to the present teachings.
Figure 19B:
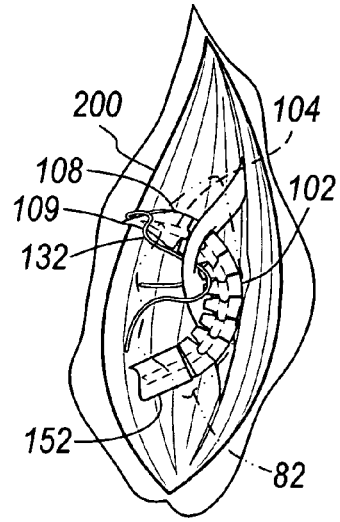
Figure 19C:
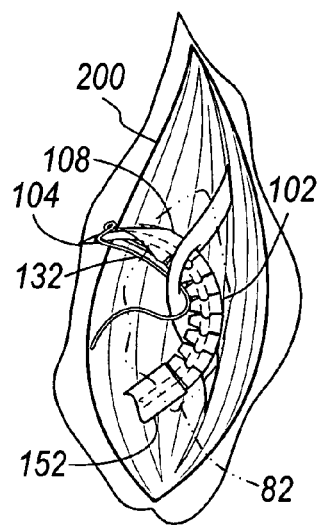
Figure 20A:
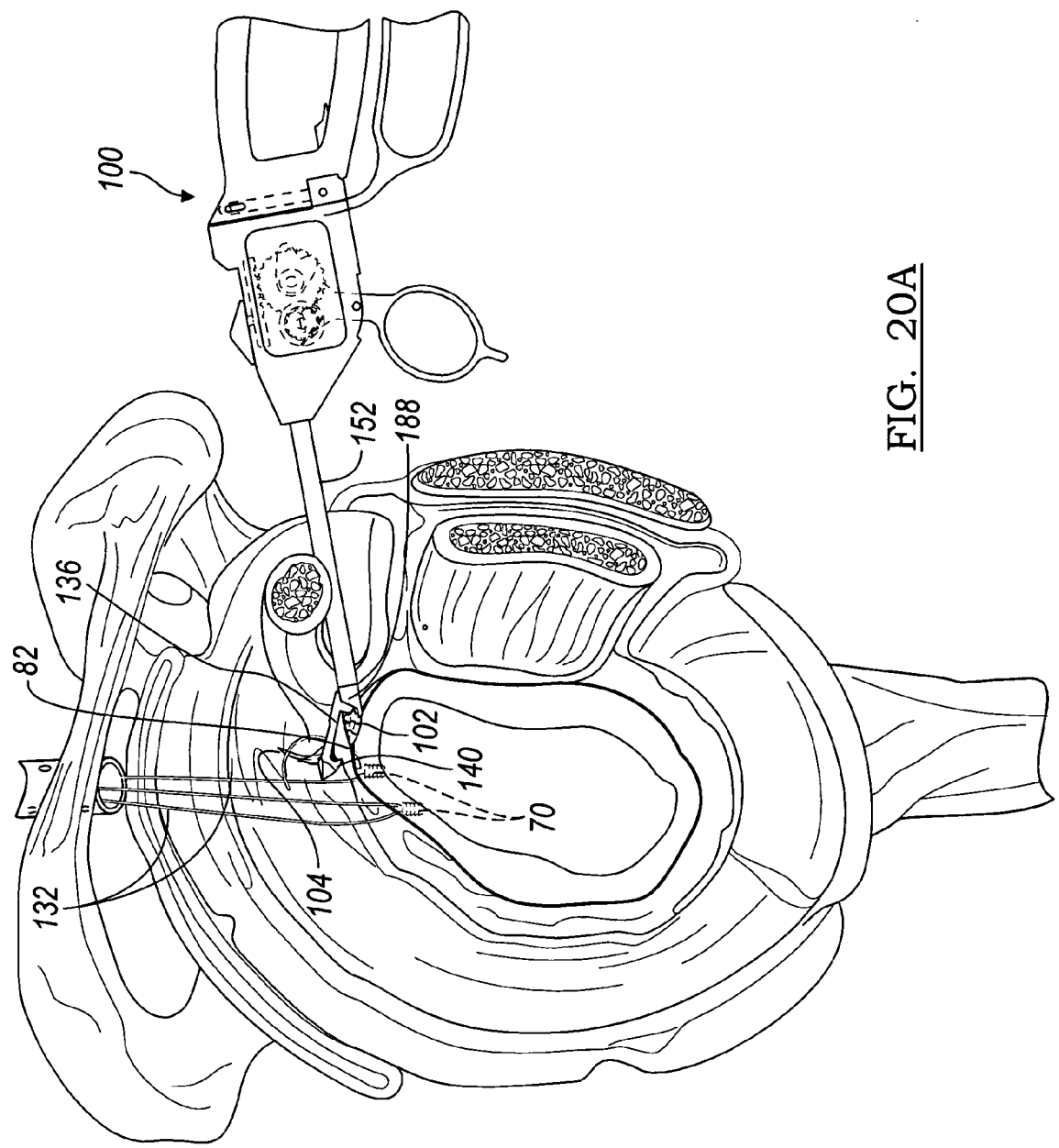
FIG. 20A illustrates a method according to the present teachings for labral lesion repair.
Figure 20B:
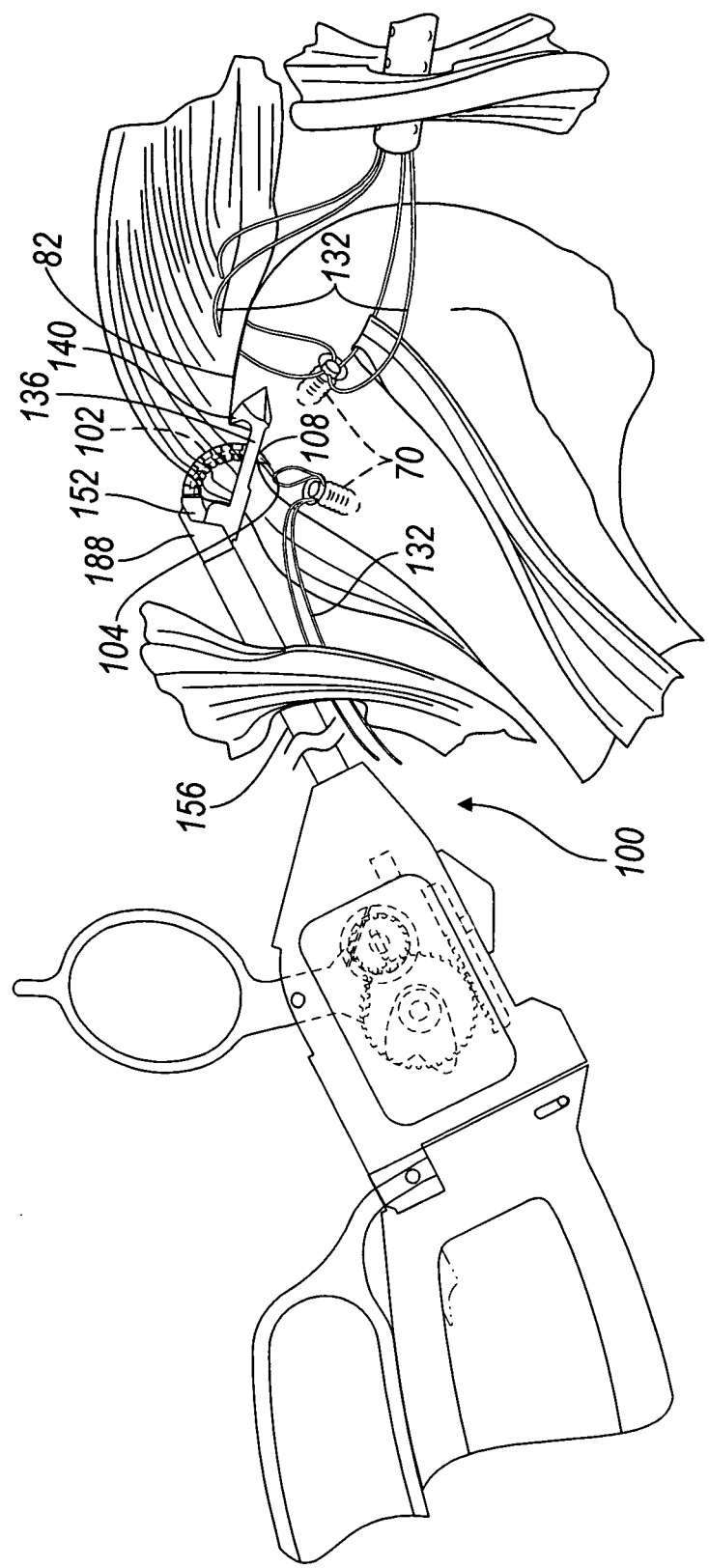
FIG. 20B illustrates a method according to the present teachings for rotator cuff repair.
Figure 20C:
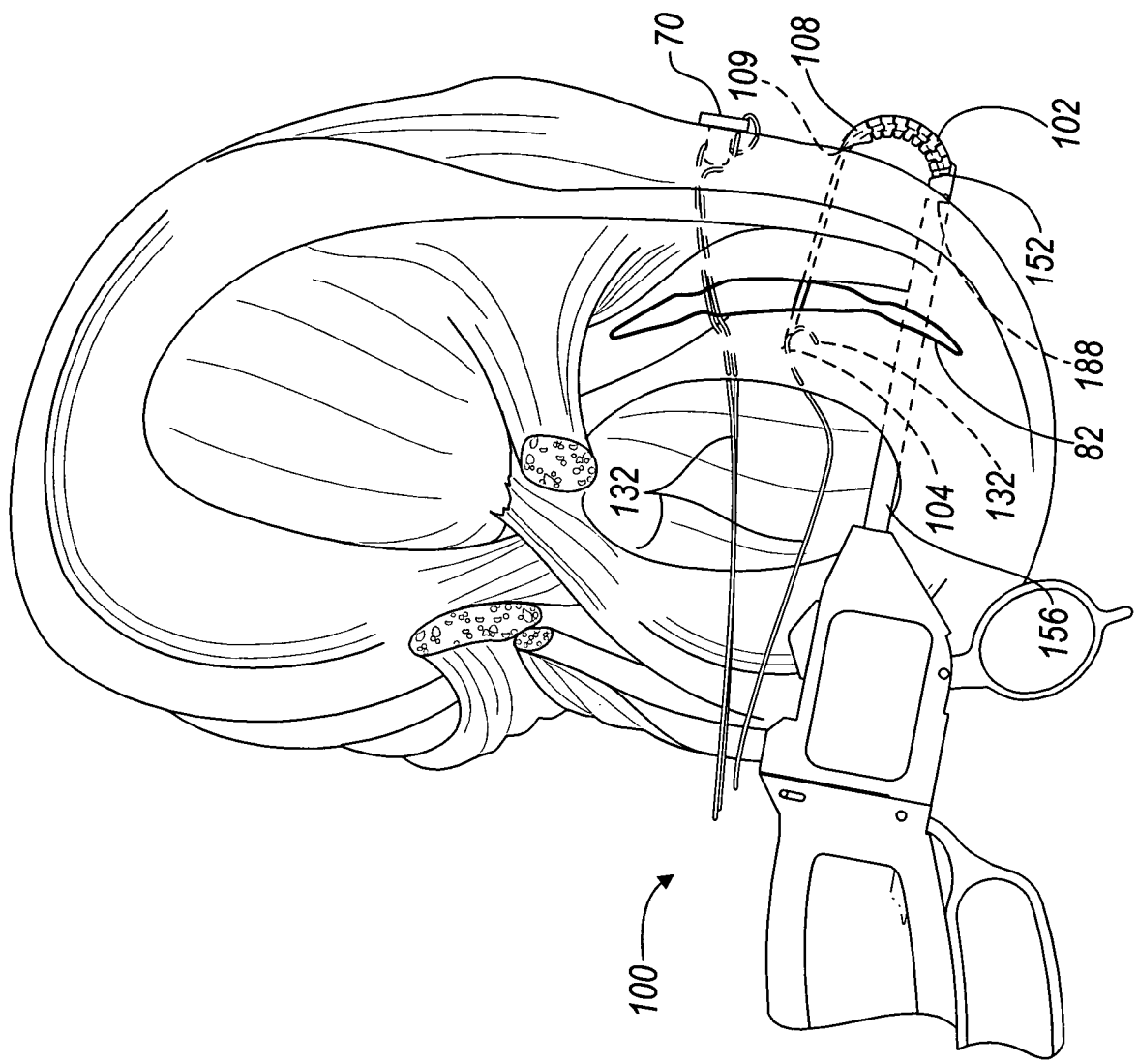
FIG. 20C illustrates a method according to the present teachings for meniscal tear repair.

Referring to FIGS. 19A-C and 20A-C, in an exemplary arthroscopic, endoscopic or other procedure requiring suturing, the bendable steerable arm 102 can be inserted in a straightened configuration through an incision 200, as illustrated in FIG. 19A. It will be appreciated that the steerable arm 102 can also be inserted in a curved configuration, as determined by the operating surgeon. The surgical procedures can include, but not limited to, rotator cuff repairs/procedures, as shown in FIG. 20B, labral repairs/procedures, as shown in FIG. 20A, meniscal repairs/procedures, as shown in FIG. 20C, or in connection with other known suture management techniques for the shoulder, knee, hip and other joint procedures, as well as other procedures of manipulating of soft tissue. The bendable steerable arm 102 can be, for example, manipulated to a desired deformed/bent/twisted configuration to pierce tissue at a desired location through or at the site of a lesion, tear, or other defect 82, as illustrated in FIG. 19B. The steerable arm 102 can be inserted through tissue with the suture holder 104 in a fully retracted position inside the bore 112 of the steerable arm 102.

Referring to FIGS. 19B and 19C, in one aspect, the tip 108 of the bendable steerable arm 102 can be loaded with a suture 132, such that a suture 132 can be passed generally through the tissue and, if indicated, through the defect 82, with the bendable steerable arm 102, as illustrated in FIG. 19B. The suture 132 can be supported on the suture-holding portion 111 of the tip 108 of the bendable steerable arm 102, shown in FIG. 12A. The suture holder 104 can be then deployed out of the bore 112 of the bendable steerable arm 102 and used to remove the suture 132 from the bendable steerable arm 102, as shown in FIG. 19C. In another aspect, the suture 132 can be also carried by the engagement feature 134 of the suture holder 104. The suture 132 can be passed back and forth through the defect 82 for repairing the defect 82. Referring to FIGS. 20A-C, the suture 132 can be coupled to a suture anchor 70, which has been implanted in the bone or tissue, depending on the procedure. After passing through the defect 82, the ends of the suture 132 can be similarly retrieved by the suture passing device 100 or by another instrument inserter through another access portal or cannula, and tied using a knot in a known manner. The process can be repeated with additional sutures 132 and anchors 70 until the defect 82 is reduced or repaired.

Referring to FIGS. 20A-B, in exemplary labral and rotator cuff procedures procedures, respectively, a suture 132 passing through an anchor 70 can be passed through tissue or retrieved from tissue with the suture passing device 100. Another suture 132 and anchor 70 are shown in connection with a different portal. Referring to FIG. 20C, exemplary meniscal procedures with and without using suture anchors 70 are illustrated. In one aspect, a suture anchor 70 can be, for example, deployed from one portal across the tear 82, and a loop of the suture 132 can be retrieved from another portal using the suture passing device 100, or another instrument (not shown). In another aspect, the suture passing device 100 can be used to deploy or retrieve a suture 132 without using an anchor. The jaw 136 can also be omitted in this procedure.

Figure 19D:
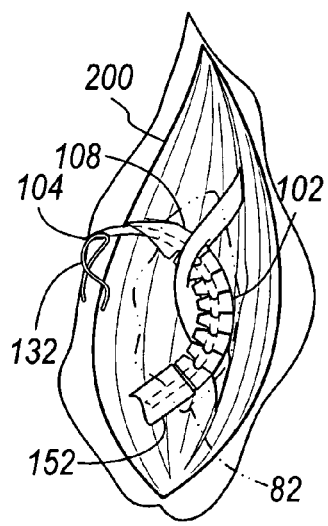

Referring to FIG. 19D, in another aspect, the unloaded (sutureless) steerable arm 102 can be passed through the tissue as described in connection with FIGS. 19A and 19B. The suture holder 104 can then be deployed to grasp an existing suture 132 and load the suture 132 onto the bendable steerable arm 102, as illustrated in FIG. 19D. The suture 132 can be passed back and forth through the defect 82 for repairing the defect 82. The exemplary procedures illustrated in FIGS. 19B-D do not involve the use the jaw 136 and can be typically, but not exclusively, employed in labral procedures.

Figure 19E:
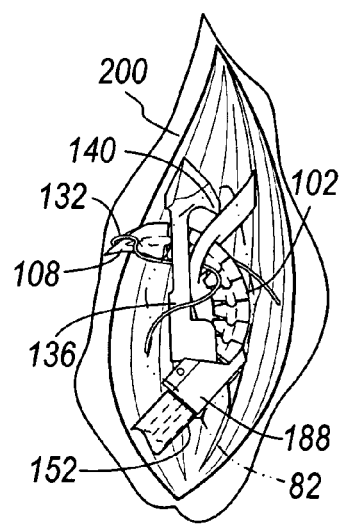
Figure 19F:
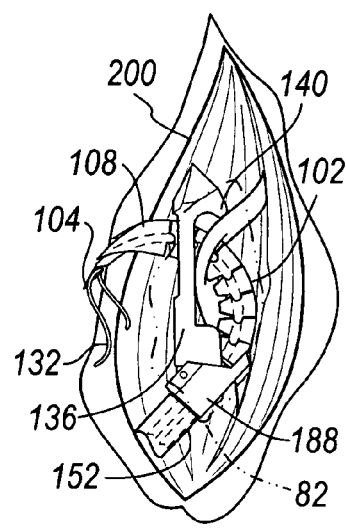

Referring to FIGS. 19E and 19F, the jaw 136 can be used to hold the tissue in a desired position, for example in connection with the procedures shown in FIGS. 19B and 19D respectively, and described above. The jaw 136, when used, can be inserted into and removed from the incision in the closed configuration, and opened as needed to grasp tissue for suturing or releasing tissue after suturing. The jaw 136 can be typically, but not exclusively, employed in rotator cuff and meniscal procedures.

It will be appreciated from the above description, that the suture holder 104 can be used as a suture retriever, suture grasper, suture passer, suture snare, depending on the procedure and as facilitated by selecting the appropriate geometric shape and size for the suture holder 104. Further, the suture-passing device 100 can be used to retrieve, or pass through tissue, a suture 132 that is coupled to a suture anchor 70, tie a suture knot and secure the suture 132.

The suture-passing device 100 of the present teachings provides a versatile instrument of compact profile that can be easily inserted through arthroscopic, endoscopic, laparoscopic or other incisions, including small incisions appropriate for minimally invasive procedures. The suture-passing device 100 can be guided by axial, pistol-grip, or other types of handles, and includes a steerable arm 102 that can be monolithic or modularly articulable. The bendable steerable arm 102 that can be deformed in two-or three-dimensional curved configurations and can also be flexed in planar or bi-planar bending and twisting. Individual link elements 106 can be rotated and pivoted relative to adjacent elements. Further, the suture-passing device 100 can be equipped with one or more suture holders 104 of different shapes and sizes for grasping, retrieving, or loading suture, and which can be deployed from the bendable steerable arm 102 functioning in cooperation with the bendable steerable arm 102. Further, a movable jaw 136 can be provided with the suture-passing device 100 for holding tissue during suturing.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A method for suturing soft tissue, the method comprising:
   inserting a bendable steerable arm in a straightened configuration through an incision, wherein the bendable steerable arm includes a plurality of interconnected links, each link having an elongated groove on a first face and an elongated projection on a second face opposite to the first face, the groove and projection defining first and second pivoting axes oriented at an angle in the range of 15-40 degrees relative to one another,
   changing the bendable steerable arm to a three dimensional curved corkscrew configuration by pivoting both the first and second pivoting axes of the bendable steerable arm;
   piercing the tissue;

deploying a suture holder from a bore of the bendable steerable arm;
moving the suture holder relative to the bendable steerable arm; and
suturing the tissue.

2. The method of claim 1, wherein suturing comprises:
carrying a suture loaded on the bendable steerable arm through the tissue; and
removing the suture from the bendable steerable arm with the suture holder.

3. The method of claim 1, wherein suturing comprises:
grasping a suture between first and second bifurcated arms of the suture holder; and
loading the suture on the bendable steerable arm.

4. The method of claim 2, wherein carrying a suture on the bendable steerable arm comprises engaging the suture with a suture holding portion of the bendable steerable arm.

5. The method of claim 1, wherein suturing the tissue comprises:
loading a suture on the suture holder; and
passing the suture through tissue with the suture holder.

6. The method of claim 5, wherein loading a suture on the suture holder comprises holding the suture in a single opening formed between first and second bifurcated arms of the suture holder.

7. The method of claim 1, wherein piercing the tissue comprises piercing the tissue with one of a tip of the bendable steerable arm or a portion of the suture holder.

8. The method of claim 1, wherein the bendable steerable arm has a central longitudinal axis when the bendable steerable arm is in the straightened configuration, and the bendable steerable arm bends around the central longitudinal axis when the bendable steerable arm is in the corkscrew configuration.

9. A method for suturing soft tissue, the method comprising:
making an incision in soft tissue;
loading a suture on a bendable steerable arm, wherein the bendable steerable arm includes a plurality of interconnected links, each link having an elongated groove on a first face and an elongated projection on a second face opposite to the first face, the groove and projection defining first and second pivoting axes oriented at an angle in the range between 15-40 degrees relative to one another;
loading a suture holder in the bendable steerable arm;
inserting the bendable steerable arm in a first configuration through the incision;
changing the bendable steerable arm to a second three-dimensional corkscrew configuration by pivoting both the first and second pivoting axes;
piercing the tissue across a defect in a first direction in the tissue;
moving the suture holder relative to the bendable steerable arm to a position at least partially outside the bendable steerable arm;
removing the suture from the bendable steerable arm with the suture holder; and
passing the suture through the defect in a second direction opposite to the first direction.

10. The method of claim 9, wherein passing the suture through the defect comprises passing the suture through one of a rotator cuff, labral, or meniscal defect.

11. The method of claim 9, wherein the first configuration is straightened, the bendable steerable arm has a central longitudinal axis when the bendable steerable arm is in the first configuration, and the bendable steerable arm bends around the central longitudinal axis when the bendable steerable arm is in the corkscrew configuration.

* * * * *